United States Patent [19]

Wu

[11] Patent Number: 4,558,697

[45] Date of Patent: Dec. 17, 1985

[54] METHOD AND APPARATUS FOR SETTING FRACTURES

[75] Inventor: Kent K. Wu, Royal Oak, Mich.

[73] Assignee: Henry Ford Hospital, Detroit, Mich.

[21] Appl. No.: 521,681

[22] Filed: Aug. 10, 1983

[51] Int. Cl.⁴ .......................... A61B 17/00; A61F 5/04
[52] U.S. Cl. .............................. 128/303 R; 128/84 C; 128/92 R
[58] Field of Search ................ 128/92 R, 92 E, 92 G, 128/20, 329 R, 329 A, 84 C, 303 R, 80 R

[56] References Cited

U.S. PATENT DOCUMENTS

| | | | |
|---|---|---|---|
| 2,543,780 | 3/1951 | Hipps et al. | 128/92 E |
| 3,585,994 | 6/1971 | Hoggler et al. | 128/303 R |
| 3,651,800 | 3/1972 | Wilbanks | 128/20 |
| 3,701,348 | 10/1972 | Navara | 128/20 |
| 3,857,386 | 12/1974 | Ashbell | 128/20 |
| 3,955,568 | 5/1976 | Neufeld | 128/92 E |
| 4,153,053 | 5/1979 | Figallo | 128/92 E |
| 4,475,549 | 10/1984 | Oh | 128/92 E |

Primary Examiner—Gene Mancene
Assistant Examiner—C. W. Shedd
Attorney, Agent, or Firm—Barnes, Kisselle, Raisch, Choate, Whittemore & Hulbert

[57] ABSTRACT

A method of setting fractures of a limb which comprises applying tension to the ends of the limb which is fractured while the limb is under X ray observation, engaging portions of the limb with hooks of tools grasped out of the range of the X ray exposure, moving the hooks transversely to manipulate the portions of the limb while the portions are under X ray observation to align the portions of the limb, and inserting a wire axially through the aligned portions.

6 Claims, 10 Drawing Figures

METHOD AND APPARATUS FOR SETTING FRACTURES

This invention relates to the setting of fractures more technically known as fracture reduction.

BACKGROUND AND SUMMARY OF THE INVENTION

In the setting of fractures particularly of limbs, a common method is to apply tension to the ends of the limb containing the broken bone while the limb is under X ray observation, manually grasping the portions of the limb and aligning the broken portions of the bone while the limb is under X ray observation and releasing the tension on the limb. It is also common to insert a wire through the aligned portions to insure proper alignment.

A serious problem with respect to such a method is that the doctor and his assistants are necessarily exposed to the radiation of the X rays.

Accordingly, among the objectives of the present invention are to provide a method and tools which will eliminate the direct exposure and thereby safeguard the health of the doctor and his assistants.

In accordance with the invention, the portions of the limb are manipulated by engaging tools having hooks with the portions of the limb adjacent the break while grasping the tools outside the range of X ray exposure and moving the hooks transversely to manipulate the portions of the limb.

DESCRIPTION

Figure 1:
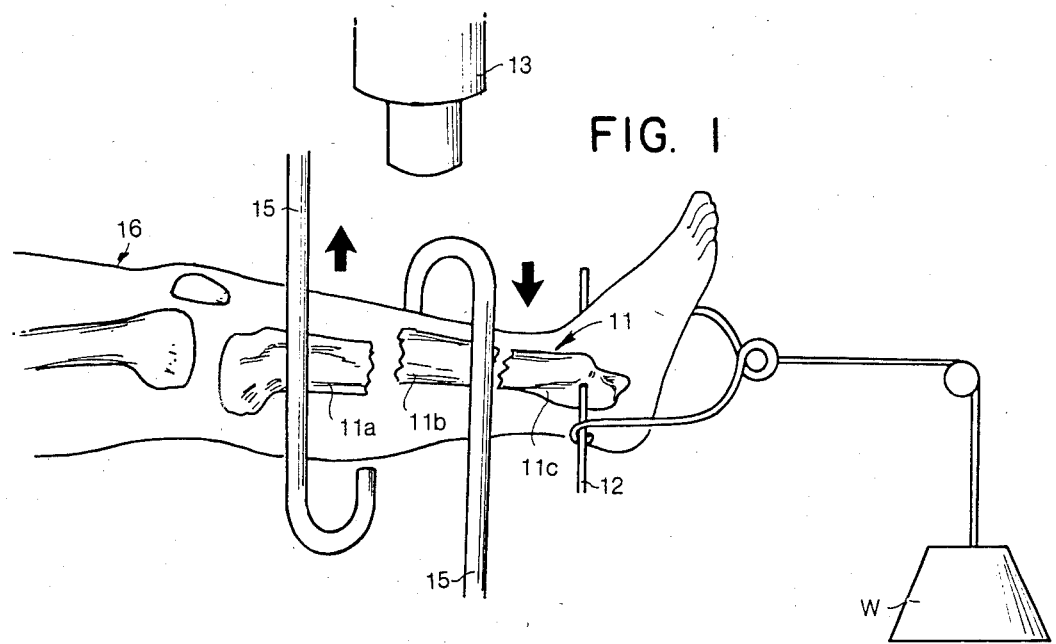
FIG. 1 is a partly diagrammatic view of an initial stage of the applicant's method.
Figure 2:
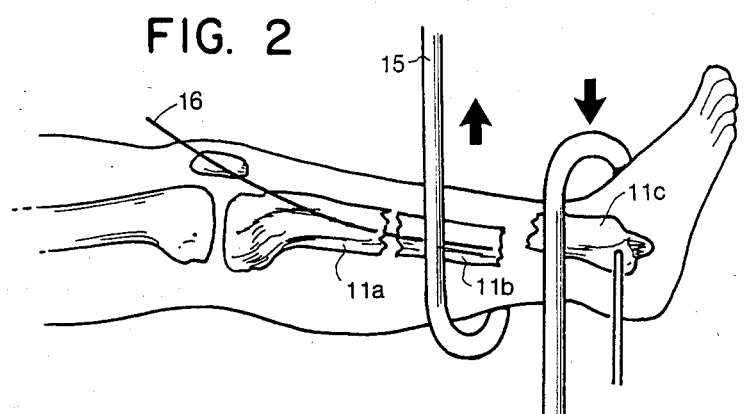
FIGS. 2 and 3 are similar views showing successive steps in the method.

Referring to FIG. 1, the method embodying the invention is shown in connection with the setting or reduction of a fracture in a limb 10 of the tibia 11. The limb 10 is placed under tension by applying a weight W to the free end of the limb as by attaching the weight to a pin 12 through the one end of the tibia 11. As shown, the tibia has two fractures. While the limb is under tension, the limb is exposed to X ray from an X ray device 13 and the doctor and his assistants can view the limb through an appropriate screen, not shown.

In accordance with the invention, hooked tools 15 are utilized to manipulate the portions of the limb and bring the broken portions of the bone 11 into alignment. As shown in FIG. 1, the tools 15 are grasped from their ends out of the range of the X ray device 13 so that the doctor and his assistants are not exposed to the radiation. The tools 15 are hooked about the leg and manipulated by movement transversely to bring the portions 11a, 11b of the bone into alignment. The tools 15 are then moved along the limb and similarly manipulated as shown by the arrows to bring the portions 11b, 11c into alignment.

Figure 3:
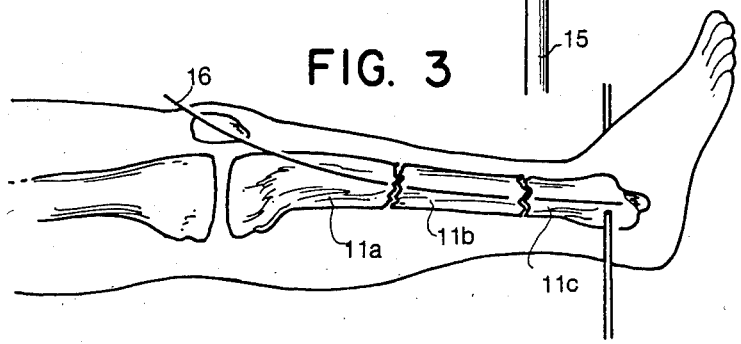

As adjacent portions are brought into alignment, a wire 16 is inserted in order to insure the proper alignment. When the tension is released as shown in FIG. 3, the bones will then be aligned.

Figure 4:
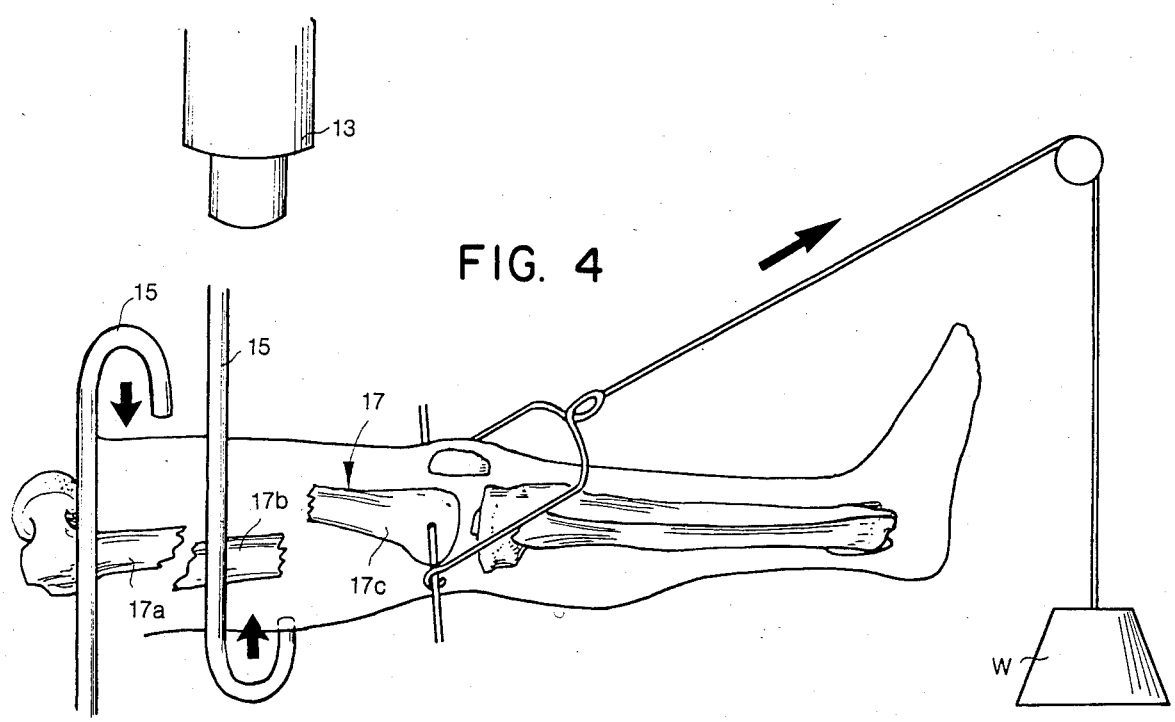
FIGS. 4, 5 and 6 show the method applied to setting the fracture of a femur.
Figure 5:
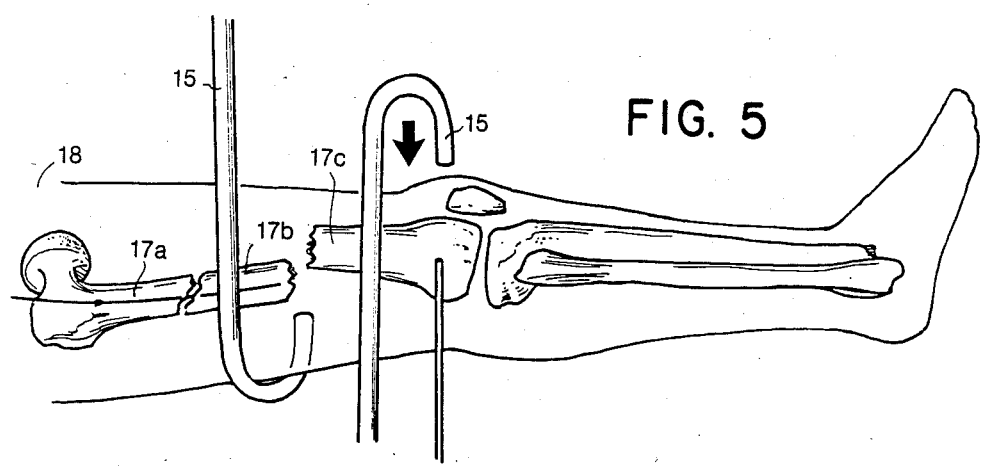
Figure 6:
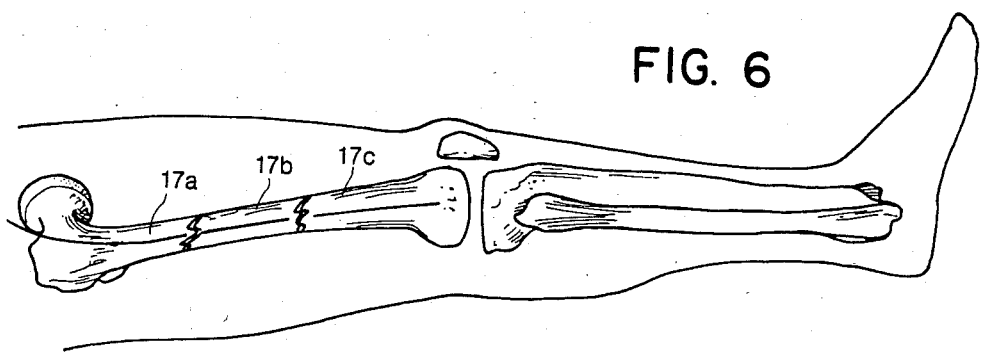

Referring to FIGS. 4, 5 and 6, the method as shown in the setting or reduction of a femur 17 herein shown as having two fractures providing bone portions 17a, b and c. As shown in FIG. 4, the tension is applied between the hip and the knee and while the tension is applied, the hooks 15 are manipulated by grasping out of the range of the radiation from opposite sides and moved transversely to first bring the portions 17a, 17b into alignment and thereafter the portions 17b and 17c (FIG. 5) into alignment. The wire 18 is then inserted and the tension released as shown in FIG. 6.

Figure 7:
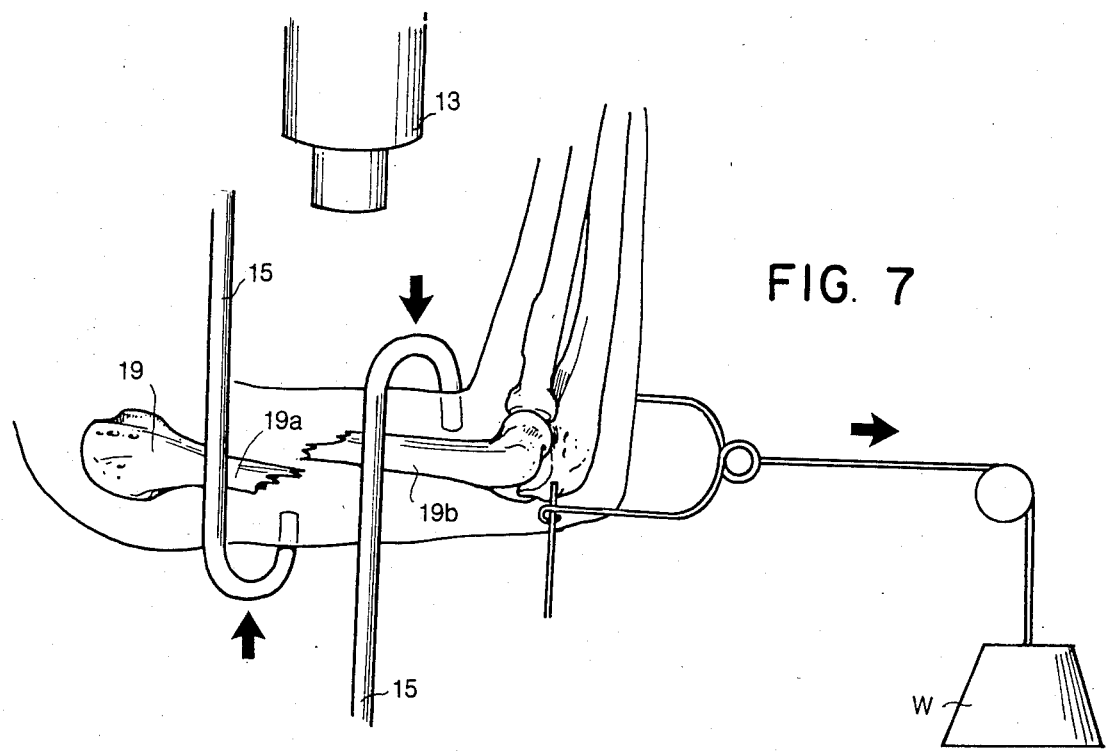
FIGS. 7 and 8 show the method applied to the setting of a humerus.
Figure 8:
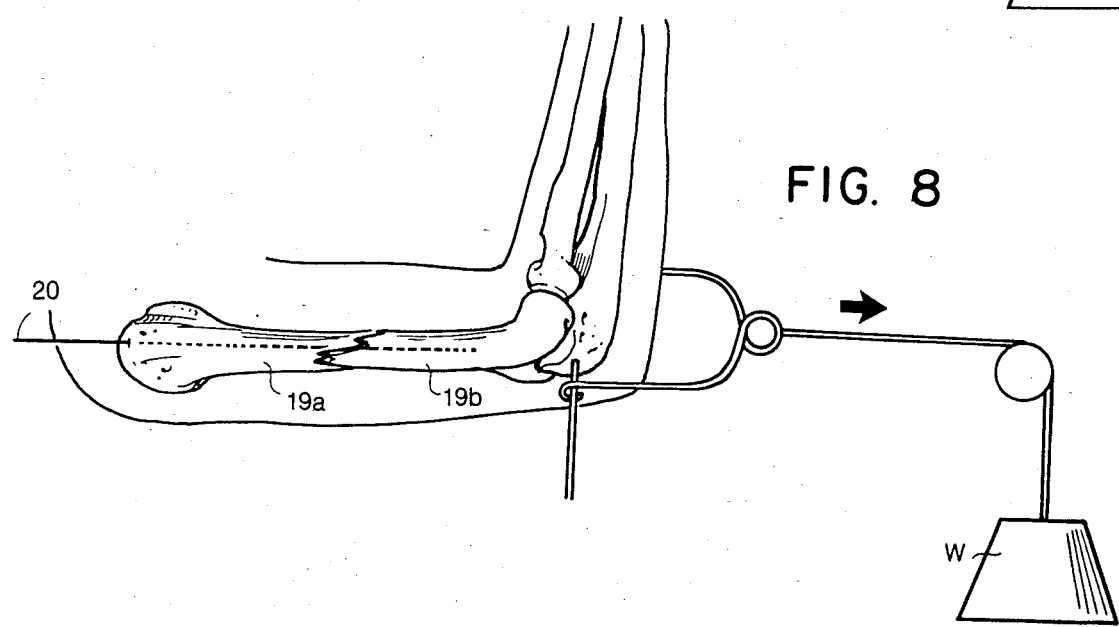

Referring to FIGS. 7 and 8, the method is shown as applied to the setting of the humerus of the arm as at 19 to bring the portions 19a, 19b into alignment. The tension is applied between the shoulder and the elbow, the hooks 15 are manipulated from opposite sides out of the radiation area, as shown in FIG. 7, bringing the portions 19a, 19b into alignment, the wire 20 is inserted and then the tension is released.

Figure 10:
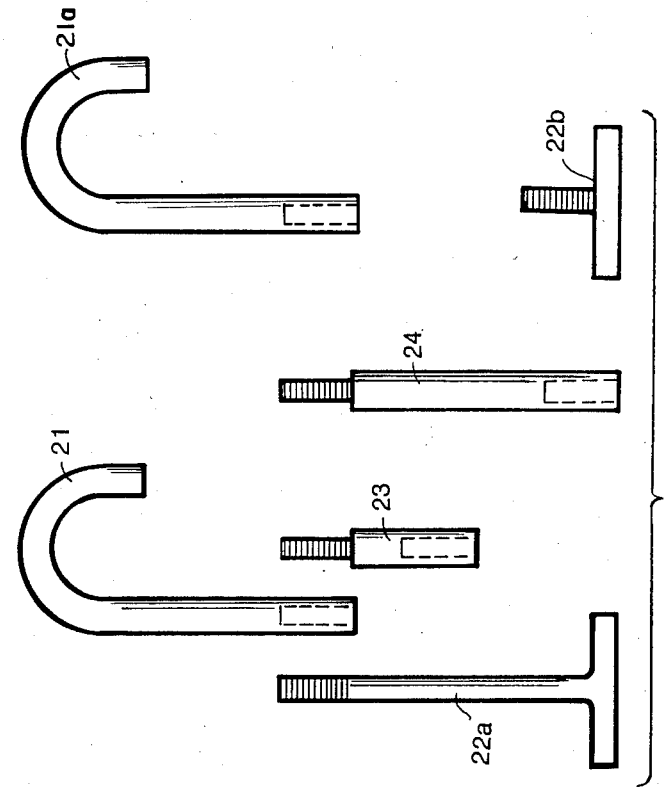
FIG. 10 is an assembly of various tools which may be utilized in the method.
Figure 9:
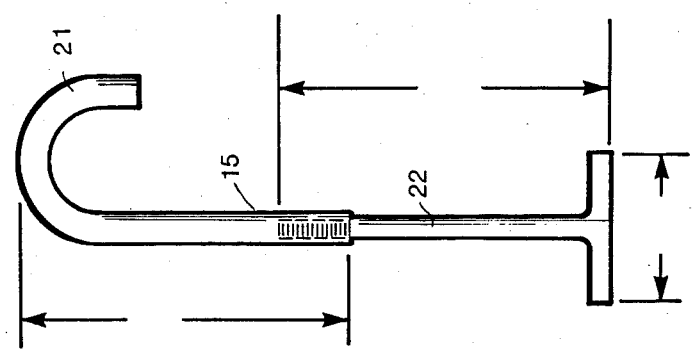
FIG. 9 is a plan view of a tool utilized in the method.

Referring to FIGS. 9 and 10, in order to provide the proper tools, a tool array or kit is provided so that the tool 15 is made of one or more parts threadedly engaged including a hook portion 21, a handle portion 22 preferably being in the form of a T, and intermediate portions 23, 24 of various lengths for extending the length of the tool. Further, the handle portions can be of various lengths such as shown at 22a, 22b. Further, the hooks 21 are preferably provided in array or kit of varying radii for engagement with wide portions of the limb as in the case of the thigh or narrow portions of the limb as in the case of an arm or lower leg.

It has been found that a hook portion with a half-inch cross section minimizes soft tissue damage.

Among the features of the invention are:

1. Minimizes the radiational exposure of the surgeons and their assistants.

2. The segmental design allows easy sterilization and storage.

3. The various hook sizes and handle lengths permit reduction of any fractured long bones (femur, tibia, fibula, humerus, radius and ulna).

4. The half-inch diameter (cross-section) of the hooks minimizes soft tissue damage when forces are applied to the extremities from various directions through these hooks.

5. The apparatus can be used in both sterile or unsterile conditions, depending on the proximity of the fracture to the operative field.

I claim:

1. In the method of setting fractures of a limb which comprises applying tension to the ends of the limb which is fractured while the limb is under X ray observation, manually manipulating the portions of the limb while it is under X ray observation to align the broken portions, and inserting a wire axially through the aligned portions, the improvement comprising
    externally engaging a first portion of the limb adjacent the fracture with a first tool having a hook sufficiently larger to encircle the first portion,
    externally engaging a second portion of the limb adjacent the fracture with a second tool having a hook sufficiently larger to encircle the second portion, manipulating the portions of the limb by grasping the tools out of the range of the X ray exposure and moving the tools transversely to manipulate the portions of the limb to align the broken portions so that the wire can be inserted.

2. The method set forth in claim 1 wherein each tool includes a handle connected thereto and the step of manipulating is accomplished by grasping said handles.

3. A tool means for setting fractured limbs while continuously monitoring the setting process by means of X ray exposure comprising an elongated portion having a hook at one end of sufficiently large arcuate extent to engage the limb externally and a handle at the other, the tool means being sufficiently long for grasping the handle out of the range of the X ray exposure area; a second tool means having a shape similar to that of said tool means for applying an opposing force to that applied by said tool means during the setting process to align the bone fragments.

4. The tool set forth in claim 3 wherein each said tool means is made of at least two parts including an array of tool parts comprising hook-parts of different radii and different lengths, T-shaped handles of different lengths and extension members of different lengths, said hook, extension, and handle parts having disengageable means for fixedly engaging same.

5. The tool means set forth in claim 4 wherein said means for disengaging the parts comprises interengaging threaded portions.

6. The tool set forth in either of claims 4 or 5 wherein the hook parts have a transverse cross section of about half an inch.

* * * * *